(12) United States Patent
Leuenberger et al.

(10) Patent No.: US 8,795,277 B2
(45) Date of Patent: Aug. 5, 2014

(54) RECONSTRUCTION DEVICE

(75) Inventors: Samuel Leuenberger, Oberdorf (CH); Jens Richter, Oberdorf (CH); Bryan James Griffiths, West Chester, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 402 days.

(21) Appl. No.: 12/680,845

(22) PCT Filed: Oct. 10, 2008

(86) PCT No.: PCT/US2008/079521
§ 371 (c)(1),
(2), (4) Date: Aug. 11, 2010

(87) PCT Pub. No.: WO2009/049161
PCT Pub. Date: Apr. 16, 2009

(65) Prior Publication Data
US 2010/0305569 A1  Dec. 2, 2010

Related U.S. Application Data

(60) Provisional application No. 60/979,562, filed on Oct. 12, 2007.

(51) Int. Cl.
*A61B 17/80* (2006.01)

(52) U.S. Cl.
USPC ............................... 606/70; 606/54; 606/254

(58) Field of Classification Search
USPC ......... 606/280, 282, 283, 284, 285, 286, 902, 606/904, 291, 254, 250, 69, 70–71; 433/172–174, 201.1; 206/343, 206/345–347, 339; 411/81, 102; 403/389–391; 24/115 R, 116 R, 116 A, 24/122.6, 128, 129 R, 130, 131 R, 135 R, 24/136 K–136 B, 115 K; 446/120, 121
See application file for complete search history.

(56) References Cited

U.S. PATENT DOCUMENTS

| | | | | | |
|---|---|---|---|---|---|
| 870,242 | A | * | 11/1907 | Meech | 403/391 |
| 1,182,980 | A | * | 5/1916 | Converse | 446/121 |
| 2,035,308 | A | * | 3/1936 | Ferber | 446/158 |
| 4,429,690 | A | * | 2/1984 | Angelino-Pievani | 606/280 |
| 5,053,036 | A | * | 10/1991 | Perren et al. | 606/291 |
| 5,704,936 | A | * | 1/1998 | Mazel | 606/254 |
| 6,136,002 | A | * | 10/2000 | Shih et al. | 606/250 |

(Continued)

FOREIGN PATENT DOCUMENTS

| | | |
|---|---|---|
| DE | 20 2007001585 U1 | 5/2007 |
| JP | 7501735 | 2/1995 |
| JP | 2002-527137 | 8/2002 |
| JP | 2007-517584 | 7/2007 |
| WO | WO 2005/069752 | 8/2005 |

*Primary Examiner* — Todd Manahan
*Assistant Examiner* — Marcela I Shirsat
(74) *Attorney, Agent, or Firm* — Baker & Hostetler LLP

(57) ABSTRACT

A bone reconstruction device (100, 200, 300) is provided that includes an elongated linkage (102, 202, 302) having a plurality of links (104, 204, 304). The reconstruction device further includes an adjustment assembly (120, 220, 320) that provides for adjustment of the directional and/or angular orientation of the links. The reconstruction device further includes a locking assembly (122, 222, 322) that is movable between a disengaged configuration and an engaged configuration. In the disengaged configuration, the adjustment assembly can be actuated to adjust the orientation of the links. In the engaged confirmation, the locking assembly inhibits adjustment of the orientation of the links.

30 Claims, 12 Drawing Sheets

(56) References Cited

U.S. PATENT DOCUMENTS

| | | | |
|---|---|---|---|
| 6,730,091 B1 * | 5/2004 | Pfefferle et al. | 606/70 |
| 6,749,612 B1 | 6/2004 | Conchy et al. | |
| 7,988,691 B2 * | 8/2011 | Schulze et al. | 606/71 |
| 2004/0039388 A1 * | 2/2004 | Biedermann et al. | 606/71 |
| 2004/0116931 A1 * | 6/2004 | Carlson | 606/70 |
| 2005/0277920 A1 * | 12/2005 | Slivka et al. | 606/61 |
| 2007/0123881 A1 * | 5/2007 | Ralph et al. | 606/69 |
| 2007/0293863 A1 * | 12/2007 | Reimels et al. | 606/69 |
| 2010/0121328 A1 | 5/2010 | Reitzig et al. | |

* cited by examiner

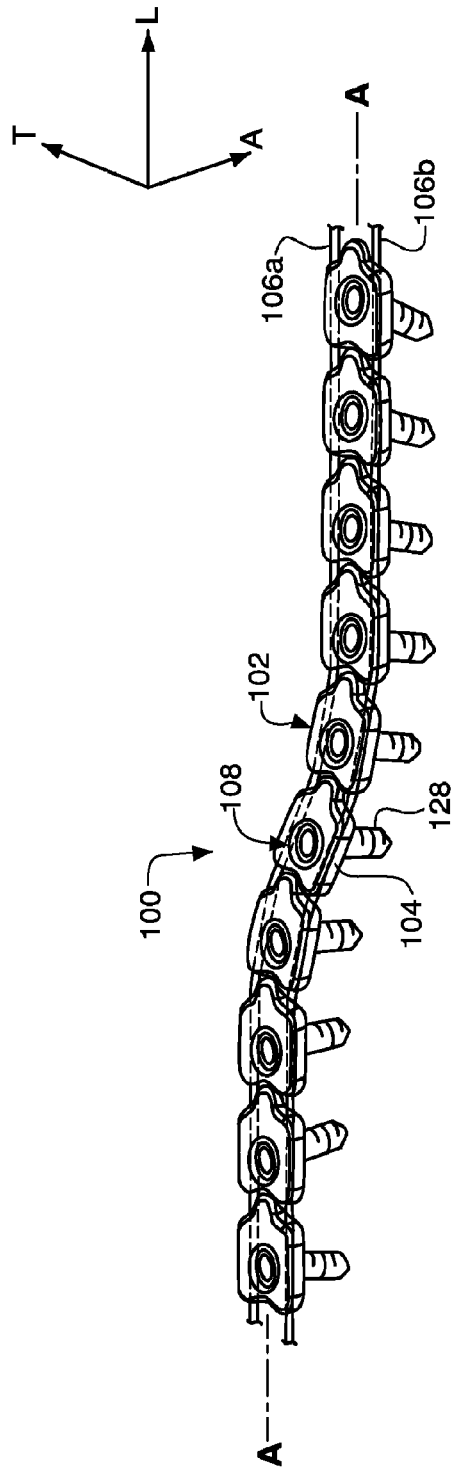
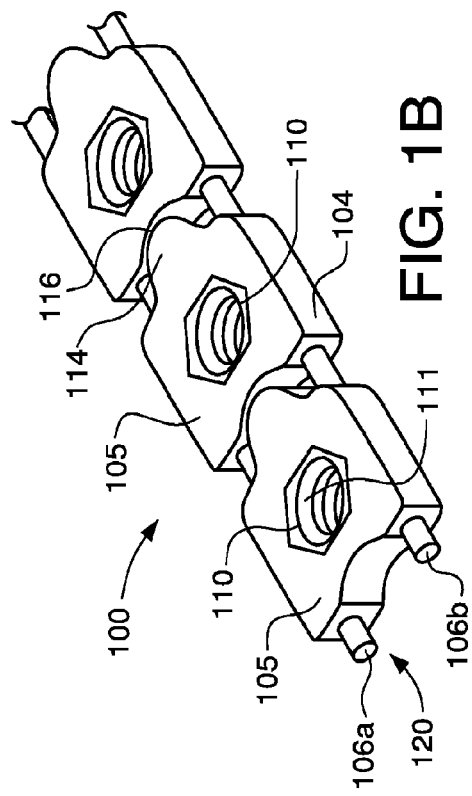
FIG. 1A
FIG. 1B

RECONSTRUCTION DEVICE

CROSS-REFERENCE TO RELATED APPLICATIONS

This application is the National Stage of International Application No. PCT/US2008/079521, filed Oct. 10, 2008, which claims the benefit of U.S. Provisional Application No. 60/979,562, filed Oct. 12, 2007, the disclosures of which are incorporated herein by reference in their entireties for all purposes.

BACKGROUND

This disclosure relates generally to bone fixation implants, and in particular relates to an adaptable bone fixation implant that can be readily shaped to repair or replace a particular bone structure of a patient.

When bones are damaged through trauma or disease, bone fixation implants are commonly used to provide anatomical reduction of bone fragments, to maintain their position after reduction, and to ensure union in the desired position. Thus, bone fixation implants are typically designed to achieve proper anatomic fit and function. Additionally, because bone fixation implants often support bones that withstand significant mechanical stress in their anatomic function, implants are often composed of strong and rigid materials. However, it is particularly difficult to fashion rigid materials to a particular patient's bone contour.

Achieving the proper shape and fit of a bone fixation implant is of particular emphasis in mandibular reconstruction. An improper fit of a mandibular fixation implant may result in disruption of the normal jaw function or alteration of the occlusion, which can cause discomfort for a patient. Additionally, it is desirable for mandibular fixation implants to be strong and rigid to provide a proper occlusion and withstand related mechanical stresses.

Prior approaches to reconstruction of a resectioned portion of the mandible include implanting a mandibular fixation device made out of metal. Unfortunately, mandibular fixation implants, such as titanium plates, must be bent to approximate the shape of the patient's mandible, which is also difficult and time consuming to accomplish. Prior approaches do not provide a bone fixation implant that can be easily and quickly modified or customized during surgery.

The need therefore exists for a bone fixation implant, formed of a rigid material, that is easy to install and customize, and that decreases the length of time the patient is in surgery.

SUMMARY

The following Summary is provided to introduce a selection of concepts in a simplified form that are further described below in the Detailed Description of Illustrative Embodiments. This Summary is not intended to identify key features or essential features of the invention, nor is it intended to be used to limit the scope of the invention. Reference is made to the claims for that purpose.

Certain embodiments are directed to a reconstruction device that, in a first state, is adaptable to various configurations and, in a second state, is set to a more rigid configuration. Thus, a surgeon can adjust the configuration of the reconstruction device, set the reconstruction device to a desired configuration, and implant the reconstruction device.

In one embodiment, the reconstruction device may include a linkage having a plurality of links that are connected to each other by a pair of connectors. Each of the links defines an aperture and two channels adjacent to the hole that can extend be parallel to each other. Each of the channels is adapted to slidably receive one of the pair of connectors and each of the holes is adapted to receive a locking member configured to impart a biasing force onto the pair of connectors and secure the plate with respect to the connectors. In a first state, the directional and/or angular orientation of at least one of the links can be adjusted with respect to each other. In a second state, the reconstruction plate is more rigidly set to a desired configuration by configuring the locking member in an engaged configuration. The reconstruction plate can further comprise a plurality of connecting elements connected between adjacent linkages. The connecting elements can be adapted to be bent to allow changes in configuration of the reconstruction plate.

In another embodiment, the reconstruction device may include a linkage having a plurality of links that are connected to each other by spine segments at one lateral end, and a connector at an opposing lateral end. Each linkage defines an aperture and a channel disposed adjacent to the hole. The channel is adapted to slidably receive the connector and the hole is adapted to receive a locking member that is configured to impart a biasing force onto the connector and secures the plate with respect to the connector. In a first state, the directional and/or angular orientation of at least one of the links can be adjusted with respect to each other. In a second state, the reconstruction plate is more rigidly set to a desired configuration by configuring the locking member in an engaged configuration.

In yet another embodiment, a reconstruction device includes a pair of linkages having a plurality of links joined by spine segments. Further, each of the links includes an aperture that is configured to receive a locking member. In a first state, the configuration of the links may be adapted by adjusting the directional or angular orientation of one or more of the links with respect to each other. The linkages can be configured to overlap such that the apertures extending through the links can be aligned. In a second state, the two reconstruction plates are coupled together to form a rigid reconstruction device by engaging a locking assembly.

According to another embodiment, methods are provided for using a reconstruction device to reconstruct a resectioned portion of a bone. Generally, the methods are directed to adapting the configuration of a reconstruction device, setting a final configuration of the reconstruction device into a more rigid state, and implanting the reconstruction device.

Additional features and advantages will be made apparent from the following detailed description of illustrative embodiments with reference to the accompanying drawings.

BRIEF DESCRIPTION OF THE DRAWINGS

The foregoing summary, as well as the following detailed description, is better understood when read in conjunction with the appended drawings. For the purpose of illustrating the reconstruction device and related method thereof, there is shown in the drawings exemplary embodiments, in which like reference numerals correspond to like reference numerals throughout. The reconstruction device and related methods are not limited to the specific embodiments and methods disclosed, and reference is made to the claims for that purpose.

FIG. 1A is a perspective view of a reconstruction device constructed as a linkage having a plurality of links in accordance one embodiment;

FIG. 1B is an enlarged perspective view of a portion of the reconstruction device illustrated in FIG. 1A;

DETAILED DESCRIPTION OF ILLUSTRATIVE EMBODIMENTS

Figure 1C:
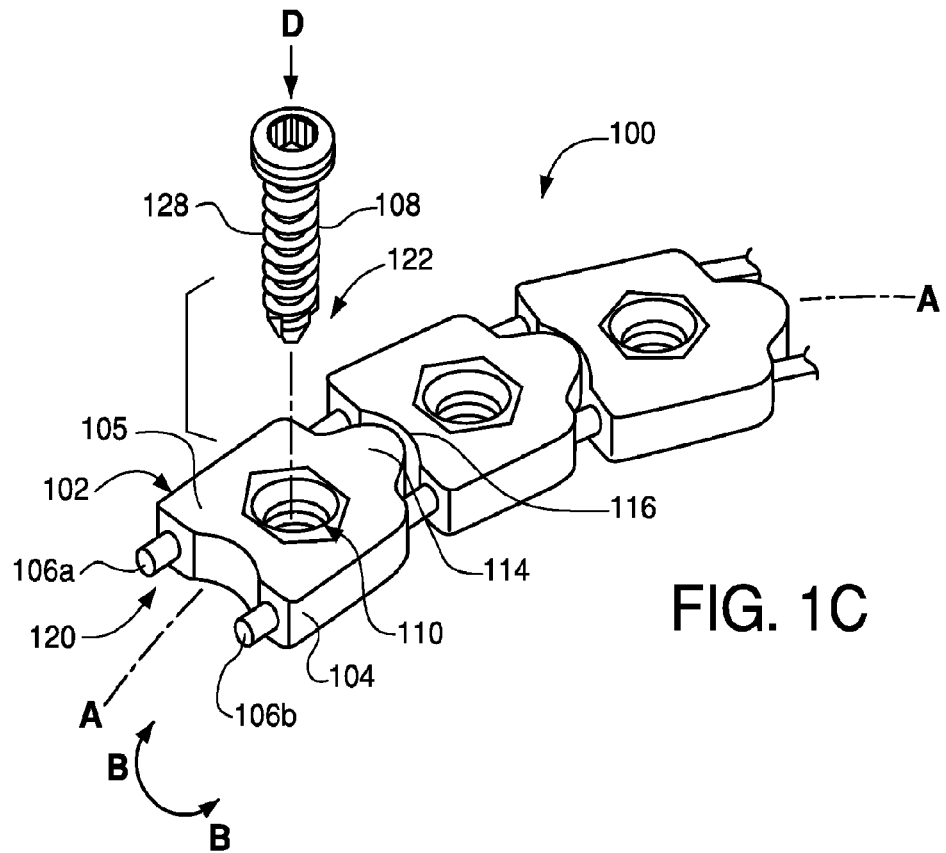
FIG. 1C is a perspective view of a portion of the reconstruction device illustrated in FIG. 1B but rotatably manipulated to a directional orientation, showing a an exploded view of a locking member.

The illustrated embodiments are directed to a reconstruction device that may be implanted to reconstruct a resected portion of a bone. The reconstruction device has particular utility as mandibular fixation implant, which requires accurate anatomical shape and fit. The reconstruction device provides adaptable shape configurations in a first state and a more rigid, final configuration in a second state. The reconstruction device comprises adaptable elements that can be set into various shape configurations. Thus, a standard reconstruction device may be customized to accommodate the particular bone structure of a patient. Biocompatible and malleable metallic materials, such as titanium, may be used to fabricate the components of the reconstruction device.

Referring initially to FIG. 1A, a reconstruction device 100 constructed in accordance with one embodiment is provided as a reconstruction linkage 102 extending along an axis of elongation A-A in a horizontal plane. The reconstruction linkage 102 can be provided as of a strip of a plurality of similarly constructed links 104 that are interconnected end-to-end via a pair of connectors 106a and 106b so as to simulate a chain link. The connectors 106a and 106b can be cut where desired to define the length of the linkage 102. The reconstruction device 100 may be made of titanium, titanium alloy, or any other suitable biocompatible material. Each link 104 attaches to a locking member 108, which can be actuated to secure the associated link 104 to the connectors 106a and 106b.

The linkage 102 and alternative linkages described throughout this disclosure extend horizontally along a longitudinal direction "L" and lateral direction "A", and vertically along a transverse direction "T". The linkages are elongate generally in the longitudinal direction L. Unless otherwise specified herein, the terms "lateral," "longitudinal," and "transverse" as used to describe the orthogonal directional components of the linkage are likewise used to describe the directional components of the remainder of the reconstruction device. Thus, the terms "inboard" and "inner," and "outboard" and "outer" with respect to a specified directional component are used herein with respect to a given apparatus to refer to directions along the directional component toward and away from the center of the apparatus, respectively.

It should be appreciated that while the longitudinal and lateral directions are illustrated as extending along a horizontal plane, and that the transverse direction is illustrated as extending along a vertical plane, the planes that encompass the various directions may differ during use, depending, for instance, on the desired directional and angular orientation of the links. Accordingly, the terms "vertical" and "horizontal" are used to describe the linkage as illustrated merely for the purposes of clarity and convenience, it being appreciated that these orientations may change during use.

Referring also to FIG. 1B, each reconstruction link 104 can include a body 105 having a generally rectangular or square with straight or curved corners, edges, and surfaces. The body 105 can define any suitable alternative geometric shape. A tongue 114, or suitable alternative protuberance, extends from one end of the body, generally along the axis A-A, and a recess 116 is formed into an opposing end of the body. The recess 116 of one link 104 is configured to abut the tongue 114 of an adjacent link 104 when the links 104 are arranged end to end, and to accommodate directional or angular movement of adjacent links with respect to each other while maintaining contact. The tongue 114 is illustrated as extending vertically and having a round convex shape and the recess 116 is illustrated as having a complementary round concave shape, the protuberance 114 and recess 116 may have any other suitable shapes as desired. The vertical outer edges of the tongue 114 prevent angular movement of adjacent links 104 about a lateral axis so as to assure proper alignment of the linkage 102.

Figure 1D:
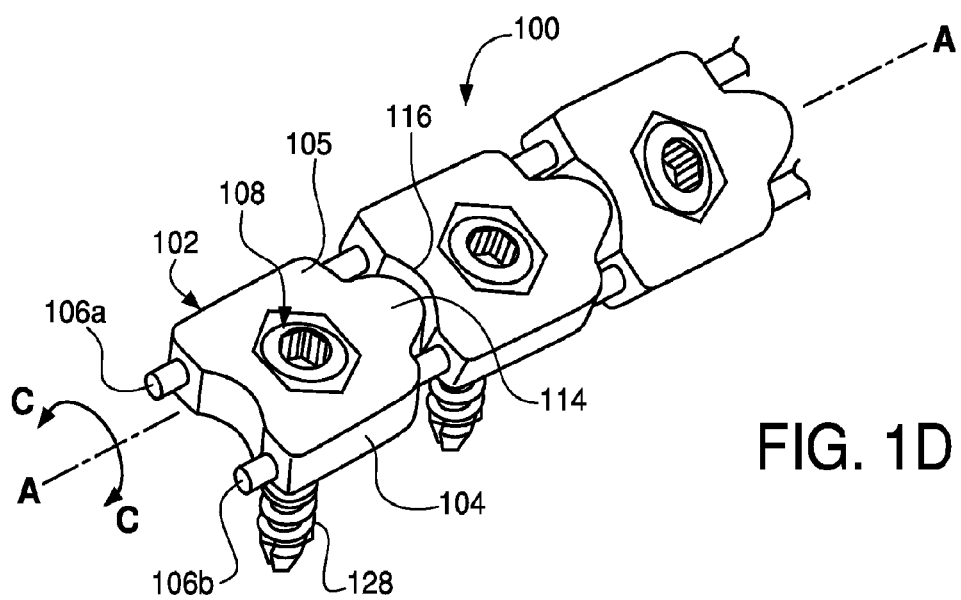
FIG. 1D is a perspective view similar to FIG. 1C, but showing the reconstruction device angularly manipulated.
Figure 1E:
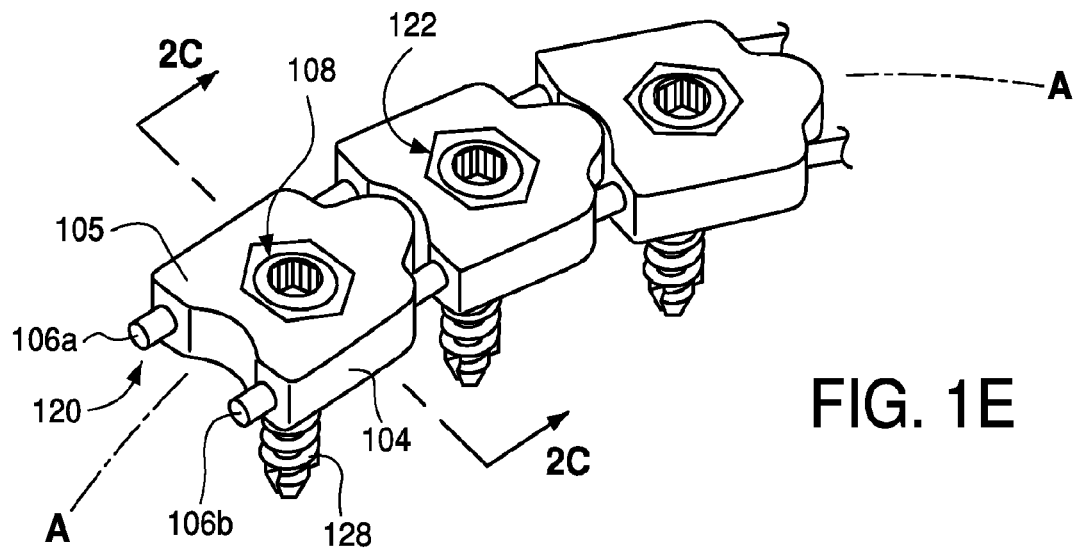
FIG. 1E is a perspective view similar to FIG. 1C, but showing the locking member in an engaged position.
Figure 1F:
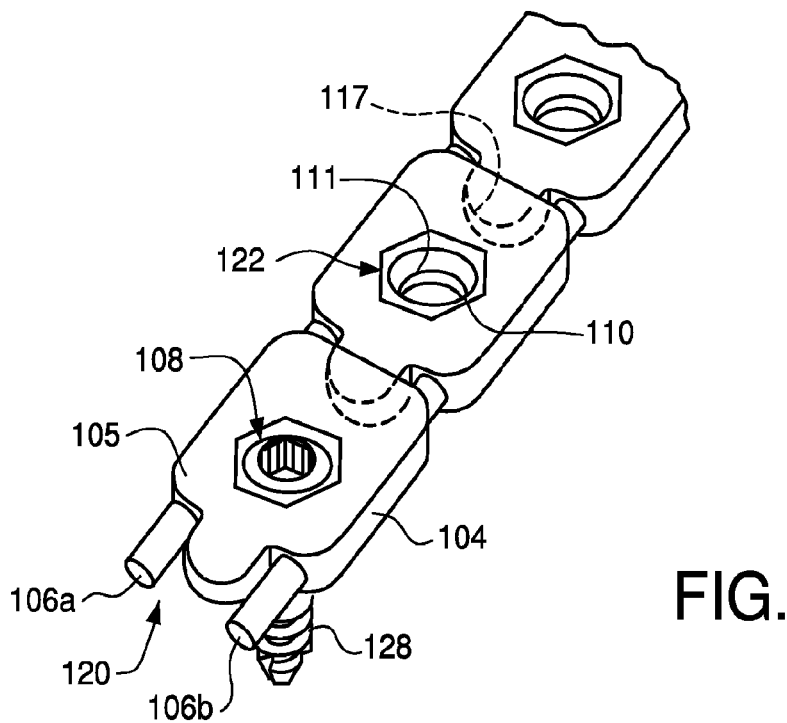
FIG. 1F is a perspective view of a reconstruction device constructed in accordance with an alternative embodiment.
Figure 1G:
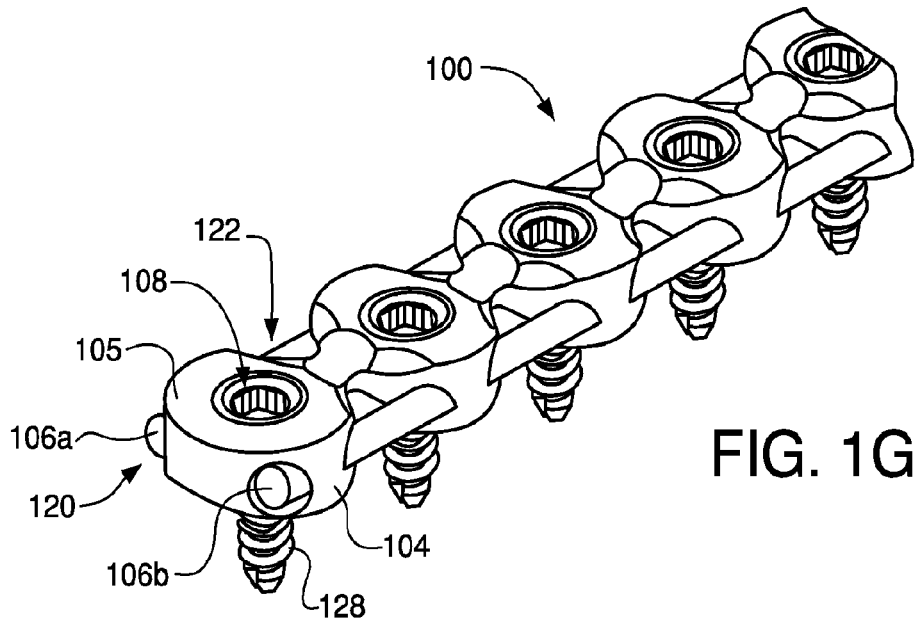
FIG. 1G is a perspective view of the reconstruction device constructed in accordance with another alternative embodiment.

Alternatively, as illustrated, in FIG. 1F, the recess can be provided as an opening 117 extending longitudinally into the body 105 that is sized and shaped to receive the tongue 114 of an adjacent link 104 so as to further interconnect the links 104. In this embodiment, the tongues 114 intersect with an adjacent link 104. Alternatively still, as illustrated in FIG. 1G, the tongue 114 of a given link 104 provides a connecting element that is attached, either integrally or via a suitable mechanical fastener, to the adjacent link 114 at a location laterally between the connectors 106. The tongues 114 are flexible so as to accommodate the bending or twisting of the links 104 to their desired directional and angular orientation.

FIG. 1B illustrates a portion of the linkage 102 elongate in a longitudinal direction. As illustrated in FIG. 1C, the connectors 106a and 106b may be provided as rods, wires, cables, threads, or other suitable structures for connecting a series of the links 104. In one embodiment, the connectors 106a and 106b are flexible so as to provide adjustment members that accommodate changes to the directional orientation of the linkage 102 as desired. In particular, when the locking members 108 are in a disengaged configuration and not attached to the links 104, the links 104 can be rotated to adjusted a directional orientation in the horizontal plane in the direction of Arrow B-B, thereby imparting lateral directional components onto the axis A-A.

Alternatively or additionally, the angular orientation of each link 104 can also be adjusted as illustrated in FIG. 1D. Specifically, each link can be rotated about the axis A-A in the direction of Arrow C-C to impart a twisted shape to the linkage 102. Once direction and orientation of the linkage 102 has been adjusted as desired, the locking members 108 can be attached to the associated links 104 to lock the direction and orientation. As illustrated, the locking members 108 are provided in the form of threaded fasteners 128, such as screws or plug screws, rivets, or any suitable alternative fasteners that can be inserted into each link 104 in the direction of Arrow D. As referenced hereinafter, a screw has a length that can extend through the link 104 and into a bone. A plug screw, as referenced hereinafter, has a length that can extend through the link but not into a bone.

Figure 2A:
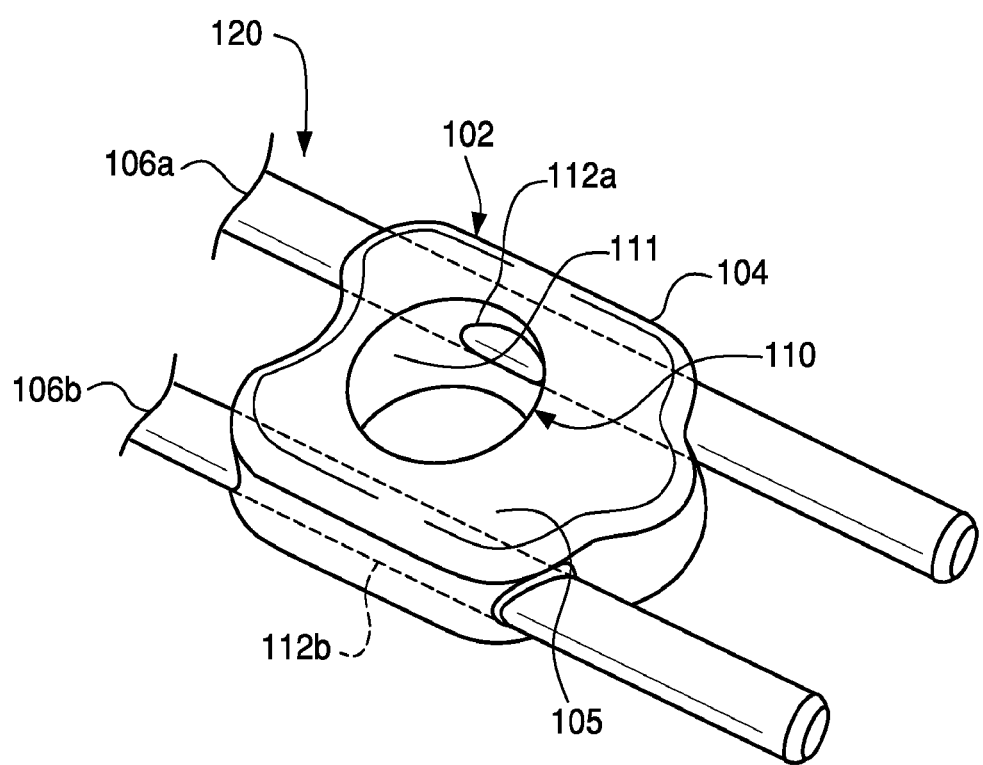
FIG. 2A is a perspective view of one of the links of the reconstruction device illustrated in FIG. 1A showing an adjustment assembly.

The adjustment of the directional and angular orientation, and subsequent locking, of the linkage 104 will now be further described with reference to FIGS. 2A-F. In particular, as shown in FIG. 2A, one or more, for instance all, links 104 includes an adjustment assembly 120 and a locking assembly 122 such that, when the locking assembly 122 is disengaged, the adjustment assembly facilitates the directional and angular manipulation of the linkage 102. When the locking assembly 122 is engaged, the distance between the laterally outer ends of adjacent links is fixed, thus locking directional and angular position of the linkages 102. In the embodiment illustrated, each link 104 incorporates a locking assembly 120 and an adjustment assembly, though it should be appreciated that only a select number of links can include the adjustment assembly 120 and locking assembly 122 as desired. Thus, in a first state, the reconstruction plate 102 is adaptable to various directional configurations and, in a second state, the reconstruction plate 102 is locked to a more rigid configuration.

Referring now to FIGS. 2A-F, the adjustment assembly 120 includes a pair of parallel channels 112a and 112b extending longitudinally through the body 105 of each linkage 104. The channels 112 are round in cross section, and are sized slightly greater than the connectors 106a and 106b, such that the connectors are slidably received inside the channels 112. Because the connectors 106 are flexible and are received loosely inside the channels 112, the directional and angular components of links 104 can be adjusted. For instance, as the lateral directional component of the links 104 changes, the connectors 106 flex laterally and slide within the channels 112, whereas when the angular directional component of the links 104 changes, the connectors flex vertically and laterally and slide within the channels 112.

Each locking assembly 122 includes an aperture 110 extending vertically through the body 105 of each link. As illustrated, the aperture is centrally disposed in the body 105 with respect to the lateral direction. The body 105 can include a rounded circumferential edge 111 that defines a portion of the perimeter of the aperture 110, and is concave with respect to the aperture 110. In one embodiment, the channels 112, connectors 106, and aperture 110 are sized and shaped such that the circumferential edge is open at its laterally outer ends and the channels 112 are partially coextensive with the aperture 110 of each link 104. In the illustrated embodiment, the laterally inner portions of the channels 112 extend into the vertical aperture 110. Accordingly, when the connectors 106a and 106b are disposed within the channels 112, the laterally inner portions of the connectors 106 likewise extend into the vertical aperture 110. In accordance with one the illustrated embodiment, the connectors 106 protrude into the aperture an equal amount.

With continuing reference to FIG. 1B, the locking assembly 122 can further include an insert 118, which can be in the form of a bushing that is sized to fit snugly within the aperture 110. The inserts 118 may be annular, oval, polygonal, or other suitable shape, and are adapted to create an interference fit with the connectors 106a, 106b in the channels 112a, 112b when the coupling elements 108 are inserted into the holes 110. The locking member 108 may be any suitable fastener configured to fix the reconstruction plate 102 to a bone.

The insert 118 can include an outer surface 124 that generally corresponds to the profile of the circumferential edge 111. The outer surface of the insert 118 thus abuts the laterally inner portions of the connectors 106. The insert 118 can be made from any suitable material that permits the insert 118 to operate as described herein. Materials including malleable biocompatible materials such as titanium, titanium alloys, or cobalt-based alloys, or elastic biocompatible materials such as ultra high molecular weight polyethylene (UHMWPE), nylon, or other thermoplastics are contemplated.

As illustrated in FIGS. 1B and 1C, the insert 118 defines a central vertical opening 126 sized to receive the locking member 120, which in one embodiment is a fastener 128 having threads 130. The insert 118 can be threaded if desired so as to mate with the threads 130 of the fastener 128. Alternatively, the opening 126 can be sized slightly smaller than the outer diameter of the threads 130, and the insert 118 can be made of a sufficiently malleable material that is capable of forming itself around the threads 130 of the fastener 128 so as to retain the fastener within the opening 126 when the fastener is inserted in to the opening 126 along the vertical direction of Arrow D.

As the fastener 128 is inserted into the opening 126, the fastener provides a biasing force that causes the bushing to expand against the connectors 106. While the biasing force is lateral, or horizontal as illustrated, it should be appreciated that the biasing force need not be purely lateral depending on the position and/or orientation of the connector 106, and can have longitudinal and/or vertical force components in addition to a lateral force component. The expansion of the bushing translates the biasing force from the fastener to the connectors 106, thereby creating an interference fit between the connectors 106, the link body 105 (and in particular the portion of the body 105 that defines the laterally outer portion of the channels 112), and the outer surface of the insert 118.

Figure 3A:
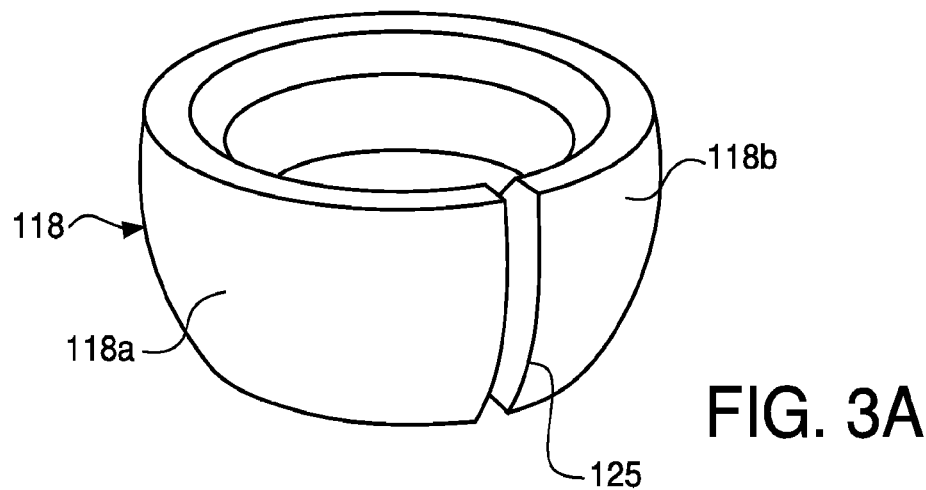
FIG. 3A is a perspective view of an insert constructed with one embodiment.
Figure 3B:
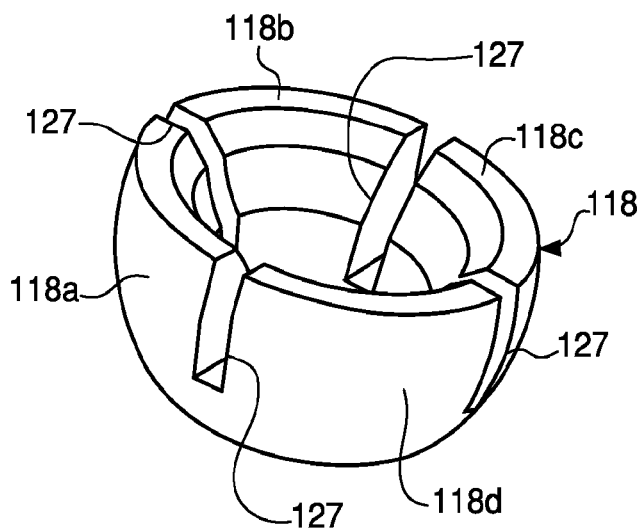
FIG. 3B is a perspective view of an insert similar to the insert illustrated in FIG. 3A but constructed in accordance with an alternative embodiment.
Figure 3C:
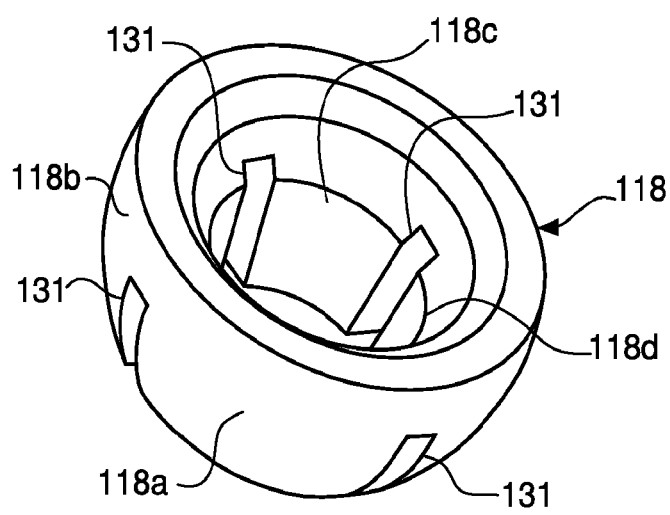
FIG. 3C is a perspective view of an insert similar to the insert illustrated in FIG. 3B but constructed in accordance with an alternative embodiment.

Referring now to FIGS. 3A-C, the insert 118 can define one or more expansion slots that divide the insert 118 into segments that can move with respect to each other as the insert 118 expands. As shown in FIG. 3A, one expansion slot 125 is formed radially through the wall of the insert 118, and extends substantially along the entire length of the insert 118 to divide the insert into segments 118a and 118b that are separated by the slot 125. In this regard, it should be appreciated that an additional expansion slot 125 can be provided, which effectively would divide the insert 118 into two discrete insert segments disposed within the opening 110 that move with respect to each other in response to the insertion of the fastener 128.

As shown in FIG. 3B, one or more expansion slots 127 is formed radially through the wall of the insert 118, and extends down from the top end of the insert 118 but terminates at a location above the bottom end of the insert. The expansion slots divide the insert 118 into insert segments 118a-d. As shown in FIG. 3C, one or more expansion slots 131 is formed radially through the wall of the insert 118, and extends up from the bottom end of the insert but terminates at a location below the top end of the insert. The expansion slots 131 divide the insert into insert segments 118a-d.

During operation, as the fastener is inserted, the thickness of the expansion slots 125, 127, and 131 expand which allows the expansion segments to deflect against the connectors in response to the biasing force imparted onto the insert 118 by the fastener 128. The expansion slots 125, 127, and 131 can be equidistantly spaced circumferentially about the insert 118, or can be spaced in any suitable alternative arrangement.

Figure 2B:
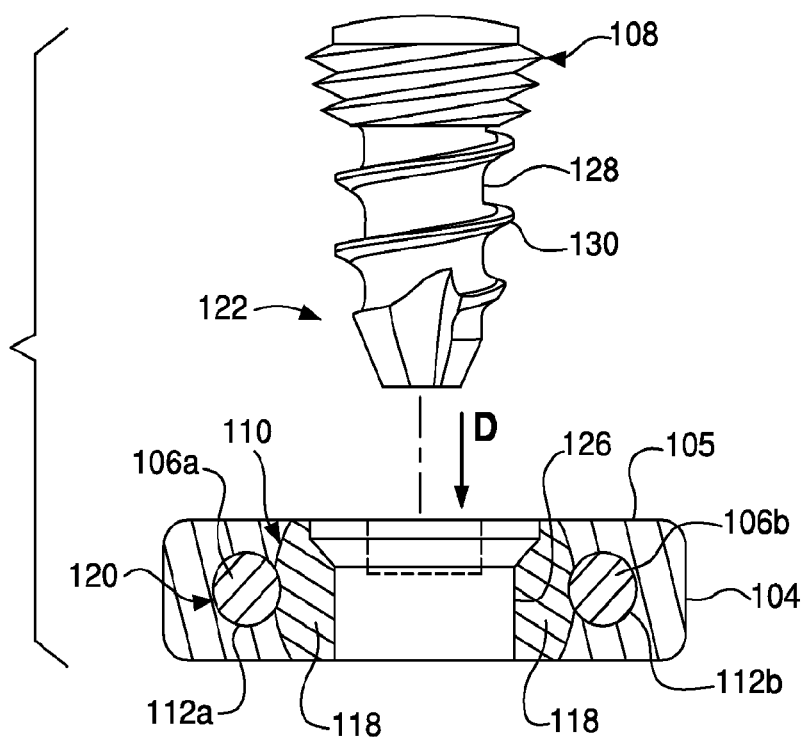
FIG. 2B is a sectional elevation view of the reconstruction device illustrated in FIG. 2A including a locking assembly in a disengaged configuration.
Figure 2C:
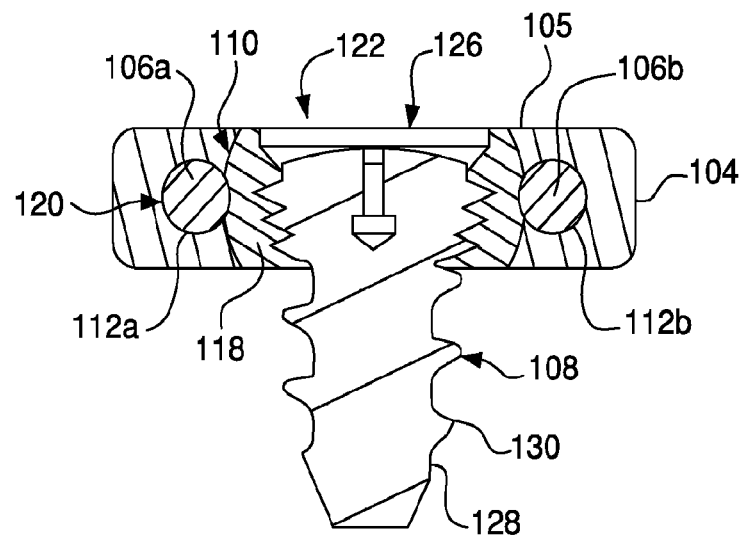
FIG. 2C is a sectional elevation view similar to FIG. 2B, taken along line 2C-2C of FIG. 1E, but showing the locking assembly in an engaged configuration.

As a result, when the fastener 128 is inserted (either partially or fully) into the opening 126 of two adjacent links 104, the connectors 106 are locked and unable to slide within the channels 112 and the directional and angular orientation of the adjacent links is locked with respect to each other. When the fastener 128 is fully inserted, the head of the fastener can either be flush with the upper surface of the link body 105, or recessed within the aperture 110 as illustrated in FIG. 2C. It should be appreciated that the fastener 128 can be tightened to an engaged configuration that increases the resistance against, but not prevent, movement of the connectors 106 (i.e., an intermediate, not fully tightened, position). Accordingly, the locking assembly 122 is operable between a disengaged configuration that allows for adjustment of the orientation of at least one of the links 104, and an engaged configuration that inhibits adjustment of the orientation of at least one of the links 104.

The fastener 128 can define a threaded shaft that has an outer threaded diameter that is substantially the same as (e.g., equal to or only slightly less than or greater than) an outer threaded diameter of the screw head, in which case the adjustment assembly 120 is locked when the fastener 128 is partially inserted into the opening 126. Alternatively, the fastener 128 can have a threaded head that has a larger threaded diameter than the shaft of the fastener, such that the adjustment assembly 120 is locked when the fastener 128 is fully inserted into the opening 126.

Figure 1H:
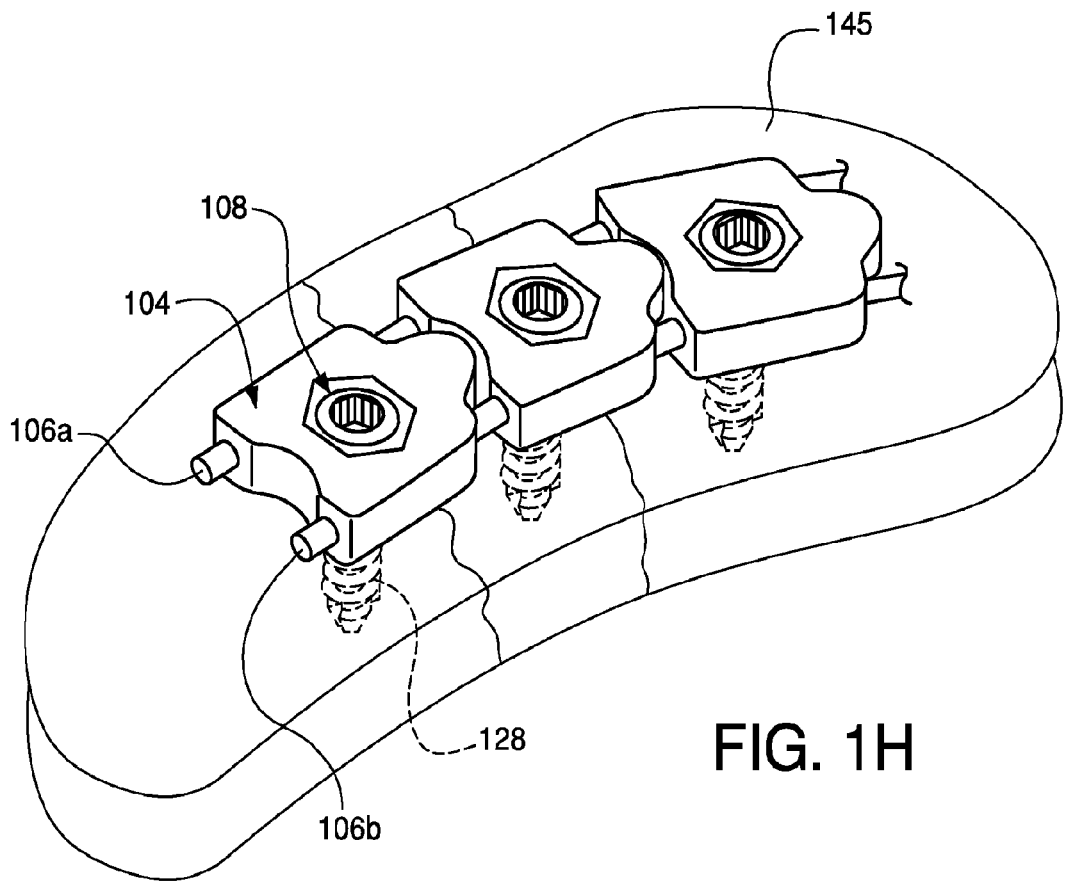
FIG. 1H is a perspective view of the reconstruction device affixed to a bone.
Figure 2D:
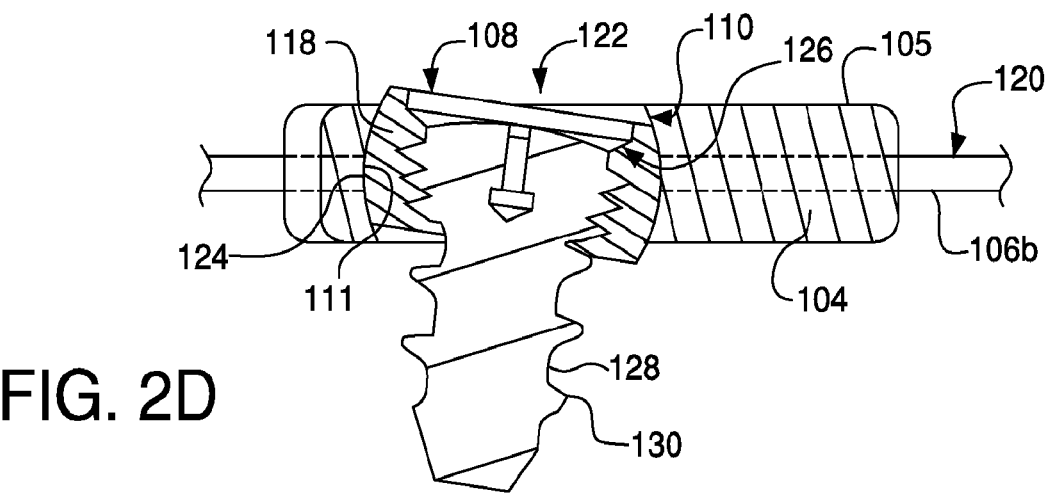
FIG. 2D is a sectional elevation view similar to FIG. 2C but showing a locking member of the locking assembly angularly displaced.
Figure 2E:
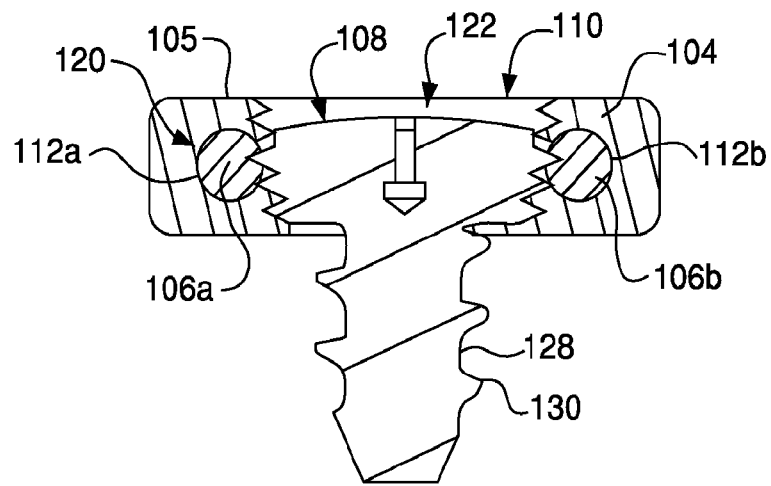
FIG. 2E is a sectional elevation view similar to FIG. 2C but showing a locking assembly constructed in accordance with an alternative embodiment.

Referring now to FIG. 2D, the rounded outer edge of the insert 118 and the circumferential edge 111 of the body 105 allows for the angular adjustment of the fastener 128 about a horizontal axis that extends longitudinally, laterally, or that has both longitudinal and lateral directional components. In particular, when the fastener 128 is partially inserted to a point before the adjustment assembly 120 is locked, the interference between the outer edge of the insert 118 and edge 111 is minimal, and the outer edge of the insert can ride along the edge 111 to adjust the angular orientation of the fastener. Accordingly, during operation, the directional and angular orientation of the linkage 104 is adjusted as desired, and the fasteners 118 are threaded into the inserts 118 at an angular orientation suitable for fixing the fastener to a bone 145 as illustrated in FIG. 1H. Once the fastener 128 has been attached to the bone 145, it has also been inserted into the opening 126 a sufficient amount to lock the adjustment assembly 120.

Preferably, the coupling elements 108 are screws or plug screws and the inserts 118 define inner surfaces having threads that mate with the threads of the screws or plug screws. As shown in FIGS. 2B-C, when a coupling element 108 is inserted, the insert 118 expands radially outward into the adjacent channels 112a, 112b to create an interference fit with the connectors 106a, 106b. Alternatively, the holes 110 channels 112a, 112b may be arranged similarly to the embodiment of FIGS. 2A and 2B, such that the heads of the screws engage and secure the connectors 106a, 106b in the channels 112a, 112b of the plate components 104. Securing the connectors 106a, 106b in the channels 112a, 112b secures the plate components 104 with respect to the connector 112 and with respect to one another.

Accordingly, in a first state, the connectors 106a, 106b are slidably disposed in the channels 112a, 112b of the plate components 104 and the reconstruction plate 102 may be adapted to various shape configurations by bending the connectors 106a, 106b and angularly or rotationally moving the plate components 104 with respect to one another. In a second state, the reconstruction plate 102 may be more rigidly set to a desired shape configuration by inserting the locking members 108 in the holes 110 of the links 104 and securing the connectors 106a, 106b in the channels 112a, 112b of the links 104.

While the locking assembly 122 has been described in accordance with one embodiment, it should be appreciated that locking assemblies constructed in accordance with alternative embodiments are contemplated. For instance, referring to FIG. 2E, the locking assembly 122 can be provided without the insert 118, such that the fastener 128 is inserted directly into the aperture 110, which is threaded and extends linearly in the illustrated embodiment, and contacts the inner portion of the connectors 106 so as to bias the connectors 106 against the link body 105 in the manner described above. In this manner, when the fastener 128 is inserted into the aperture 110, the interference with the connectors 106 locks the adjustment assembly 120. It should thus be appreciated that the fastener 128 provides a locking member that imparts a biasing force, either directly or indirectly, onto the connectors 106.

Figure 2F:
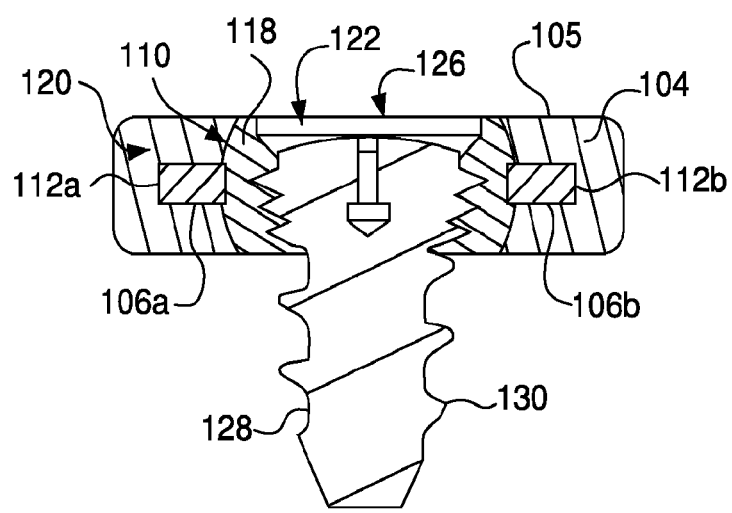
FIG. 2F is a sectional elevation view similar to FIG. 2A, but showing the adjustment assembly constructed in accordance with an alternative embodiment.
Figure 2G:
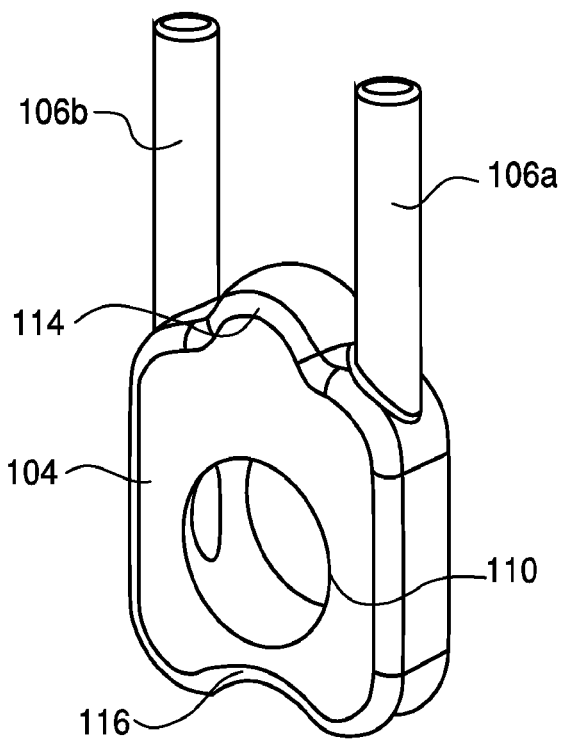
FIG. 2G is a sectional elevation view similar to FIG. 2A, but showing the adjustment assembly constructed in accordance with another alternative embodiment.

Furthermore, while the adjustment assembly 120 has been described in accordance with one embodiment, it should be appreciated that adjustment assemblies constructed in accordance with alternative embodiments are contemplated. For instance, the connectors 106a and 106b can be provided as a rod or tube having any desired cross sectional profile to adjust the stability of the directional and angular orientations of the linkage 102, or to set the ease with which the links 104 can be adjusted in a given orientation. As illustrated in FIG. 2F, the connectors 106 can have a rectangular profile having lateral and vertical directional components, and can be elongate in the lateral direction. Alternatively, the connectors 106 can be elongate in the vertical direction. Alternatively still, the connectors 106 can have a square, oval, polygonal, or other suitable cross sectional shape, such that they are able to slide within the respective channels 112 when the locking assembly 122 is disengaged, and are configured to lock in position when the locking assembly 122 is engaged. Alternatively still, the connectors 106a, 106b can be integrally formed with one or more links 104 as illustrated in FIG. 2G.

While the reconstruction device 100 and its alternative embodiments have been illustrated and describe above, it should be appreciated that the a reconstruction device is not intended to be limited to the embodiment described above, and that other alternative embodiments are contemplated. One such alternative embodiment is illustrated in FIGS. 4A-F.

Figure 4A:
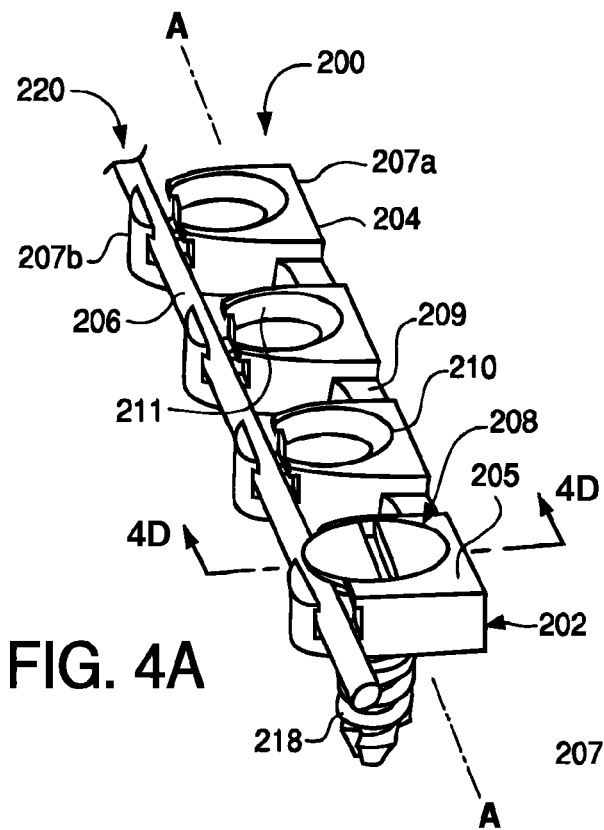
FIG. 4A is a perspective view of a reconstruction device constructed in accordance with an alternative embodiment.

In particular, FIG. 4A illustrates a reconstruction device 200 constructed in accordance with an alternative embodiment as including a linkage 202 extending along an axis of elongation A-A in a horizontal plane. The reconstruction linkage 202 can be provided as an elongate strip of material having cutouts to form a plurality reconstruction links 204 each having a body 205. Each body 205 includes opposing lateral ends 207a and 207b. Lateral ends 207a are interconnected to adjacent links 204 via spine segments 209 that are integrally formed with the linkage 202, and extend between adjacent links 204, while a connector 206 connects the outer lateral ends 207b of each link 204. While the spine segments 209 are integrally formed with the linkage 202 in accordance with one embodiment, it should be appreciated that the spine segments 209 could alternative be connected to the links 204 via any suitable mechanical fastener. The connector 206 and spine segments can be cut where desired to define the length of the linkage 202.

The reconstruction device 200 may be made of titanium, titanium alloy, or any other suitable biocompatible material. Each link 204 attaches to a locking member 208 (illustrated as being installed in one of the links 204 of the linkage 202), which can be actuated to secure the associated link 204 to the connector 206.

Figure 4B:
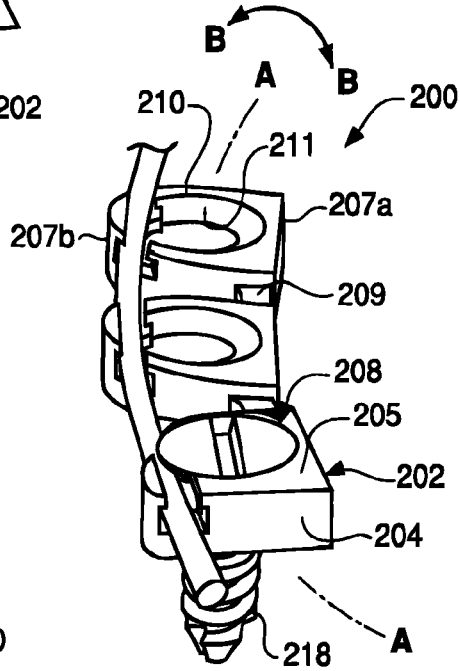
FIG. 4B is an enlarged perspective view of a portion of the reconstruction device illustrated in FIG. 4A but rotatably manipulated.
Figure 4C:
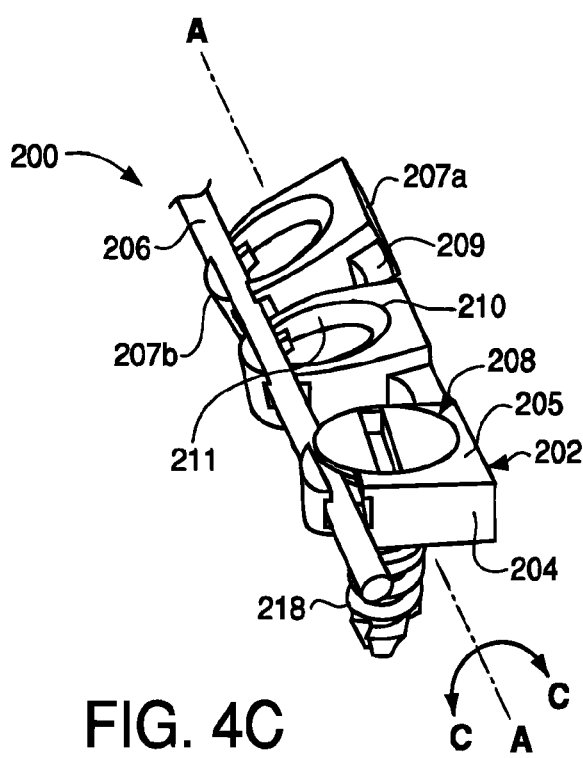
FIG. 4C is a perspective view similar to FIG. 4B, but showing the reconstruction device angularly manipulated.

Referring also to FIG. 4B, the connector 206 may be provided as a rod, wire, cable, thread, or other suitable structures for connecting a series of the links 204. In accordance with the illustrated embodiment, the connector 206 and spine segments 209 are flexible so as to provide adjustment members that accommodate changes to the directional orientation of the linkage 202 as desired. In particular, when the locking members 208 are in a disengaged configuration and not attached to the links 204, the links 204 can be rotated to adjusted a directional orientation in the horizontal plane in the direction of Arrow B-B, thereby imparting lateral directional components onto the axis A-A.

Alternatively or additionally, the angular orientation of each link 204 can also be adjusted. Specifically, each link can be rotated about the axis A-A in the direction of Arrow C-C to impart a twisted shape to the linkage 202. Once direction and orientation of the linkage 202 has been adjusted as desired, the locking members 208 can be attached to the associated links 204 to lock the direction and orientation. As illustrated, the locking members 208 are provided in the form of threaded fasteners 228, such as screws or plug screws, that can be inserted into each link 204 in the direction of Arrow D. Thus, in a first state, the reconstruction plate 102 is adaptable to various directional configurations and, in a second state, the reconstruction plate 102 is locked to a more rigid configuration.

Figure 4D:
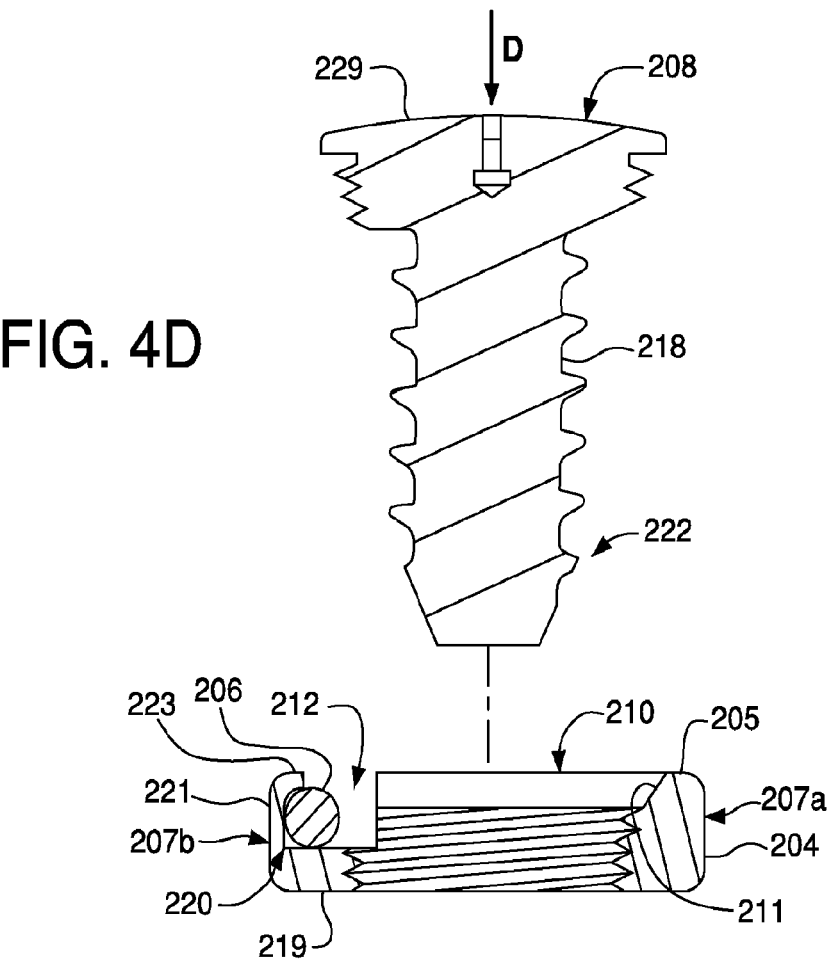
FIG. 4D is a sectional elevation view of the reconstruction device illustrated in FIG. 4A taken along line 4D-4D, showing a coupling device configured for installation.

The adjustment of the directional and angular orientation, and subsequent locking, of the linkage 204 will now be further described with reference to FIGS. 4D-E. In particular, as shown in FIG. 4D, one or more links 204 includes an adjustment assembly 220 and a locking assembly 222 such that, when the locking assembly 222 is disengaged, the adjustment assembly facilitates the directional and angular manipulation of the linkage 202. When the locking assembly 222 is engaged, the distance between the laterally outer ends of adjacent links is fixed, thus locking directional and angular position of the linkages 202. In the embodiment illustrated, each link 204 incorporates a locking assembly 220 and an adjustment assembly, though it should be appreciated that only a select number of links can include the adjustment assembly 220 and locking assembly 222 as desired.

Figure 4E:
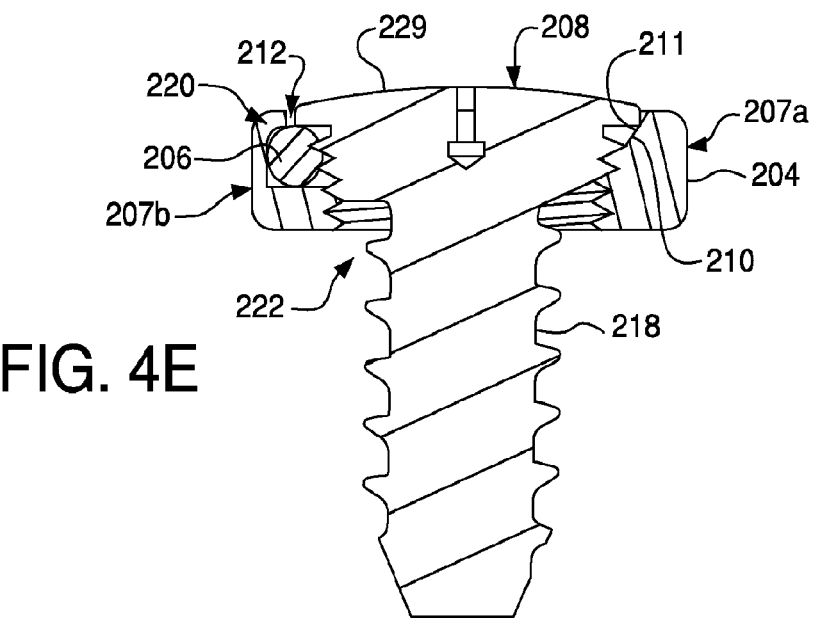
FIG. 4E is a sectional elevation view of the reconstruction device similar to FIG. 4D but showing the coupling device installed.

Referring now to FIGS. 4D-E, the adjustment assembly 220 includes a channel 212 defined at the outer lateral end 207b of each link 204. In particular, the outer lateral lend 207b includes a laterally outwardly projecting base 219 that defines the bottom end of the channel 212, a flange 221 that extends up from the laterally outer end of the base 211 that defines the laterally outer end of the channel 212, and a lip 223 that projects laterally inwardly from the upper end of the flange 221 that partially defines an upper end of the channel 212.

The channel 212 is sized slightly greater than the connector 206 such that the connector is slidably received inside the channel 212. Because the connector 206 is flexible and are received loosely inside the channel 212, the directional and angular components of links 204 can be adjusted. For instance, as the lateral directional component of the links 204 changes, the connectors 206 flex laterally and slide within the channel 212, whereas when the angular directional component of the links 204 changes, the connectors flex vertically and laterally and slide within the channel 212.

Each locking assembly 222 includes an aperture 210 extending vertically through the body 205 of each link 204. As illustrated, the aperture 210 is centrally disposed in the body 205 with respect to the lateral direction. The body 205 can include a circumferential edge 211 that defines at least a portion of the perimeter of the aperture 210. The circumferential edge 211 can be threaded so as to be configured to receive the threaded fastener 228.

In one embodiment, the channel 212, connector 206, and aperture 210 are sized and shaped such that the channel 212 is partially coextensive with the aperture 210 of each link 204. In the illustrated embodiment, the laterally inner portion of the channels 212 extends into the vertical aperture 210. Accordingly, when the connectors 206 are disposed within the channel 212, the laterally inner portions of the connector 206 likewise extends into the vertical aperture 210. In accordance with the illustrated embodiment, the connector 206 protrudes into the aperture an equal amount. Alternatively, the edge 211 can define the entire perimeter of the aperture 210, such that the channel 212 is positioned adjacent and separate with respect to the aperture 210.

With continuing reference to FIGS. 4D-E, the locking assembly 222 includes the threaded fastener 228 that is threadedly received in the aperture 210. The fastener 228 includes a head 229 that extends laterally to a position that is in at least partial alignment with the connector 206. As a result, as the fastener 228 is inserted into the aperture 210, the fastener head 229 comes into contact with the upper portion of the connector 206. Further tightening of the fastener 228 causes the locking assembly 222 to assume an engaged configuration, whereby the fastener head 229 imparts a downward biasing force directly onto the connector which creates an interference fit between the connector 206, the base 219, and the fastener head 229.

While the biasing force is transverse, or vertical as illustrated, it should be appreciated that the biasing force need not be purely transverse depending on the position and/or orientation of the connector 206, and can have longitudinal and/or lateral force components in addition to the transverse force component.

As a result, when the fastener 228 is inserted into the aperture 210 of two adjacent links 204, the connector 206 becomes locked and unable to slide within the channel 212 and the directional and angular orientation of the adjacent links 204 is locked with respect to each other. It should be appreciated that the fastener 228 can be tightened to an intermediate position (i.e., not fully tightened), so as to increase the resistance against, but not prevent, movement of the connector 206.

Accordingly, during operation, the directional and angular orientation of the linkage 204 is adjusted as desired, and the fasteners 218 are threaded into the apertures at an. The fastener 228 is inserted into the bone until the screw head sufficiently abuts the connector 206 so as to lock the connector in place. The fastener 228 is elongated a sufficient amount such that it becomes reliable anchored in the bone. Alternatively, the aperture 210 is not threaded, and is sized greater than the shaft of the fastener, such that the fastener 228 is screwed directly into the bone until the screw head 229 locks the connector 206 in place.

Alternatively, the locking assembly can include an insert of the type described above with reference to the reconstruction device 100 that expands in response to insertion of the fastener 228 so as to lock the connector 206 with respect to movement relative to the links 204.

Thus, the reconstruction device 200 can achieve a first state, in which the connector 206 is slidably disposed in the channels 212 of the links 204, and the linkage 202 can be adapted to various shape configurations by bending or twisting the spine segments 209 and connector 206, thus moving the links to a desired directional and angular orientation when the locking assembly 222 is in a disengaged configuration. In a second state, the locking assembly 222 is engaged, and the links 204 are more rigidly set to a desired shape configuration by inserting the fasteners 228 into the apertures 210 of the plate links 204 and securing the connector 206 in the channels 212 of the links. Securing the connector 206 in the channels 212 not only secures the links 204 with respect to the connector 206, but also more rigidly secures the links 204 with respect to one another. Thus, in a first state, the reconstruction plate 200 is adaptable to various configurations and, in a second state, the reconstruction plate 200 is set to a more rigid configuration.

Figure 5A:
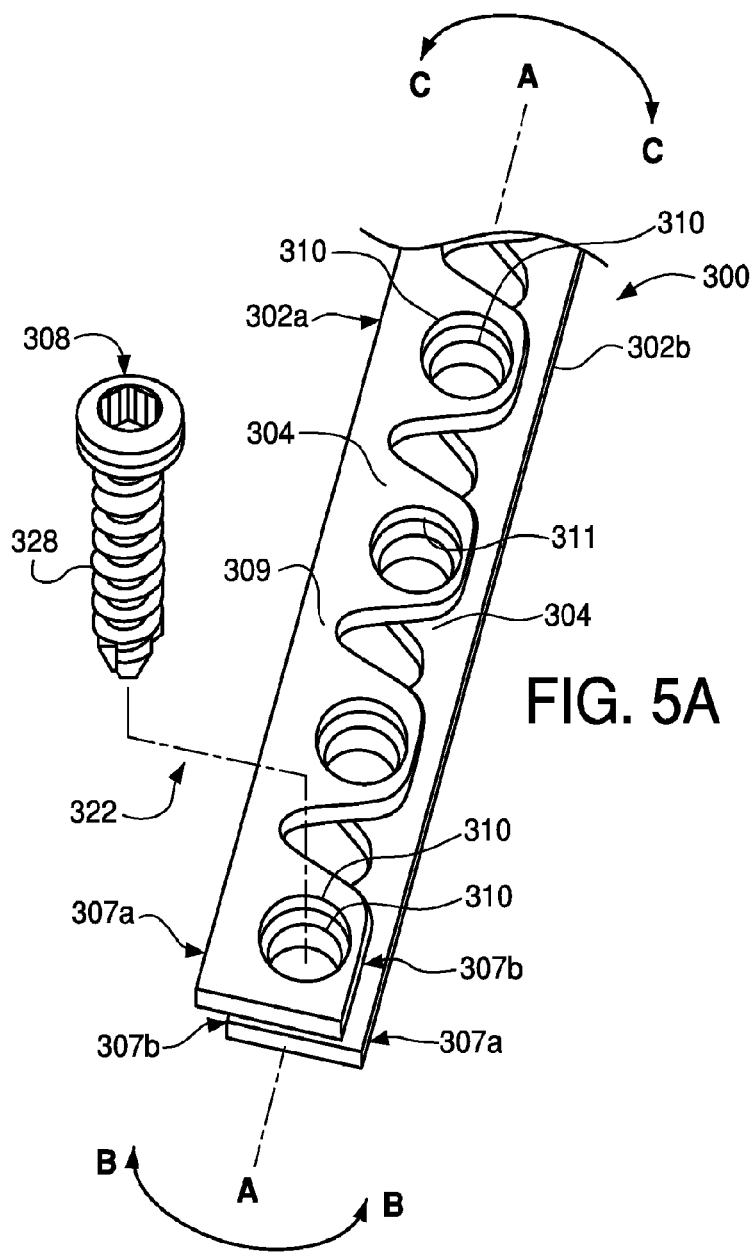
FIG. 5A is a perspective view of a reconstruction device constructed in accordance with still another alternative embodiment.
Figure 5B:
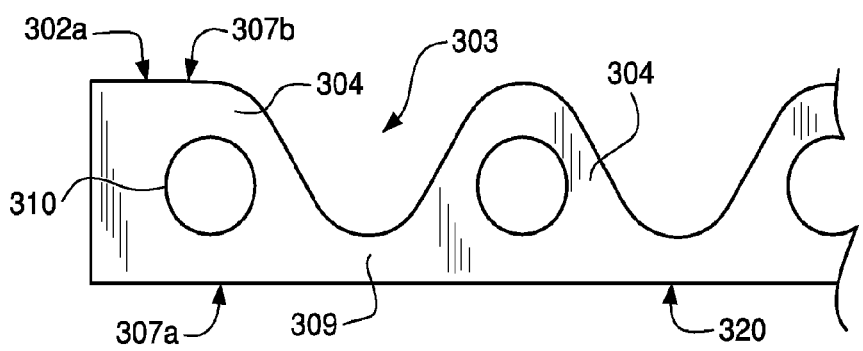
FIG. 5B is a top plan view of one of the reconstruction plates illustrated in FIG. 5A.

Referring now to FIGS. 5A-B, a reconstruction device 300 constructed in accordance with an alternative embodiment includes a pair of similarly constructed linkages 302a and 302b. The reconstruction device 300 may be made of titanium, titanium alloy, or any other suitable biocompatible material. Each linkage 302 can include an elongate strip of material having a plurality of links 304 that defines opposing lateral ends 307a and 307b. Each link 304 of the linkages 302 is interconnected by a spine 309 at one lateral end 307a. The spine 309 can be integrally formed with each linkage as illustrated, or can be connected via a suitable mechanical fastener. Each linkage 302 further includes a plurality of notches 303 cut into the opposing lateral end 307. The notches can be curved, for instance parabolic, as illustrated, or can assume any suitable alternative shape as desired. Each linkage 302 defines an aperture 310 extending vertically through each link 304. The aperture can be threaded so as to threadedly receive a threaded fastener 328, or can be unthreaded, and sized to receive the threaded fastener 328.

The linkages 302a and 302b are configured to be fixedly coupled to each other by overlapping the linkages 302 such that the lateral end 307a of one of the linkages is on the same lateral side of axis A-A of the lateral end 307b of the opposing linkage. In this configuration, the spine 309 of one linkage 302a opposes the spine 309 of the opposing linkage 302b. The linkages 302a and 302b extend parallel to each other such that the apertures 310 are aligned.

The reconstruction device 300 includes an adjustment assembly 320 that accommodates changes to the directional and angular orientations of the linkages 302 as desired, and a locking assembly 322 that is configured to achieve a disengaged configuration that provides for the adjustment of the orientations and an engaged configuration that prevents adjustment of the orientations.

In particular, the adjustment assembly 320 is actuated by bending the spine 309, which provides an adjustment member, in the horizontal plane in the direction of Arrow B-B, thereby imparting lateral directional components onto the axis A-A. Furthermore, spine 309 can be rotated about the axis A-A in the direction of Arrow C-C to impart a twisted shape to the linkage 302. Once the directional and angular orientations have been achieved, the apertures 310 can be aligned and the orientations can be fixed with the locking assembly 322.

In this regard, it should be appreciated that the linkages 302a and 302b can be constructed differently with respect to each other. For instance, the apertures 310 extending through the links 304 of the linkage 302a can be sized differently (for instance oversized or undersized) with respect to the apertures extending through the links 304 of the linkage 302b. Accordingly, when the links 304 of the linkages 302a and 302b are directionally and/or angularly manipulated, the apertures 310 of the linkages 302a and 302b overlap a sufficient amount such to facilitate insertion of the fastener. In this regard, the fastener 328 can be inserted through both aligned apertures 310 prior to manipulating the directional and angular orientations of the linkages 302a and 302b. If the apertures 310 of the upper linkage 302a are oversized, then the fastener 328 is threaded into the apertures 310 of the lower linkage 302b, while the head of the fastener is configured to engage the upper linkage 302a and provides a biasing force that retains the linkages 302a and 302b in a fixed position.

The locking assembly 322 includes a locking member 308 in the form of threaded fasteners 328 (one shown in FIG. 5A) that are sized for insertion into each aperture 310. If the apertures 310 are threaded, the threads of each aligned aperture 310 are also aligned so as to provide continuous threads that are configured to receive the fastener 328. Alternatively, the openings 310 are not threaded, and are sized only slightly greater than the diameter of the fasteners 328. Accordingly, the fasteners 328 are received in the associated apertures 310 such that the outer surface of the fasteners 328 makes light contact with the edges 311 that define the apertures 310, thereby preventing further changes to the directional or angular orientation of the linkages 302.

Furthermore, the fastener 328 includes a head 329 that extends laterally to a position that is in at least partial alignment with the upper linkage 302. As a result, as the fastener 328 is inserted into the apertures 310, the fastener head 329 comes into contact with the upper linkage 302. Further tightening of the fastener 328 causes the locking assembly 322 to assume an engaged configuration, whereby the fastener head 329 imparts a downward biasing force onto the upper linkage 302 which creates an interference fit between the linkages 302, the bone, and the fastener head 229. As a result, when the fastener 328 is inserted into the apertures 310 of the overlapping linkages 302, the links 304 of each linkage 302 becomes locked with respect to directional and angular movement. It should be appreciated that the fastener 328 can be tightened to an intermediate position (i.e., not fully tightened), so as to increase the resistance against, but not prevent, movement of the links 302.

Alternatively, the fasteners 328 can be loosely received in the apertures 310, such that insertion of the fasteners 328 into the apertures 310 does not engage the locking assembly 322. Rather, the insertion of the fastener 328 into the bone causes the locking assembly 322 to engage in the manner described above.

Thus, in a first state, the reconstruction linkages 302a and 302b are not fixedly coupled to each other and each can be adapted to various shape configurations by bending or twisting the spine 309 and angularly or rotationally moving the links 304 with respect to one another. In a second state, the linkages 302a and 302b are fixedly coupled to each other to form a more rigid configuration. Thus, in a first state, the reconstruction device 300 is adaptable to various configurations and, in a second state, the reconstruction device 300 is set to a more rigid configuration. While the reconstruction device 300 has been described as including a pair of linkages 302a and 302b, it should be appreciated that the device 300 could alternatively include more than a pair of linkages 302a and 302b that are configured and operate in the manner described above.

In another embodiment, and as described above, it should be appreciated that a kit can be provided that includes all or a portion of any of the reconstruction devices described herein. For example, the kit can include one or more of the components of the reconstruction device 100, or any of the reconstruction devices disclosed herein. The one or more components included in various kits can have one or more varying characteristic such as size and/or shape. For instance, a first kit can be provided having one or more components, for instance links 104, connectors 106a and 106b, inserts 118, and/or fasteners 128 of the reconstruction device 100 of one size or shape, and one or more other kits kit can include the same one or more components as the first kit, but of a size and/or shape that is different from those in the first kit to accommodate different mandibular sizes and shapes, or to accommodate different mandibular reconstruction procedures. Alternatively or additionally, a kit can include a plurality of the same component of the reconstruction device, but of different sizes and/or shapes. For instance, a kit can include a plurality of links 104, connectors 106a and 106b, inserts 118, and/or fasteners 128, of varying sizes and/or shapes. The components can be stored and later assembled into a reconstruction device, thereby imparting flexibility onto the construction of the reconstruction device, which can be suited to the particular nature of a given mandibular reconstruction.

According to another embodiment, methods are provided for implanting the various embodiments of the reconstruction device. Generally, the methods include the steps of adjusting an orientation (e.g., directional or angular) of a reconstruction device, setting a final configuration of the reconstruction device into a more rigid state, and implanting the reconstruction device. It is to be understood that certain steps of the methods described herein can be omitted, combined, performed simultaneously, or performed in a different order. In this regard, it should be appreciated that the reconstruction devices of the type described above can be provided as a kit that is configured to be implemented for the purposes of bone reconstruction using the methods described below.

According to one method of reconstructing a resectioned portion of a bone, the configuration of the reconstruction device 100, as shown in FIGS. 1A-1G and 2A-2G, may be adapted by adjusting the directional and/or angular orientation of the links 104 with respect to one another to achieve a desired shape and fit for a bone reconstruction in the manner described above. The orientation can be adjusted by actuating the adjustment assembly 120. Thus the configuration of the reconstruction device 100 may be adapted to achieve the proper shape and fit for a bone reconstruction. The final configuration of the reconstruction device 100 may be set more rigidly by actuating the locking assembly 122 to an engaged configuration, whereby the fasteners 128 are instead into the apertures 110 of the linkages 104. The reconstruction device 100 can then be implanted by inserting the fasteners 128 into a bone. In accordance with aspects of the method, the fasteners 128 can provide the dual purpose of locking the adjustment assembly 120 and becoming implanted into the bone.

According to another method of reconstructing a resectioned portion of a bone, the configuration of the reconstruction device 200, as illustrated in FIGS. 4A-E, may be adapted by moving the links 204 with respect to one another in the manner described above to achieve a desired directional and angular orientation. The orientation can be achieved by actuating the adjustment assembly 220. Thus the configuration of the reconstruction device 200 may be adapted to achieve the proper shape and fit for a bone reconstruction. The final configuration of the reconstruction device 200 may be set more rigidly by actuating the locking assembly 222, for instance by inserting locking members in the form of fasteners 228 into the apertures 210 of the links 204, and securing the connector 206 in the channels 212 of the plate links 204. The reconstruction device 200 can then be implanted by inserting the fasteners 228 into a bone. In accordance with aspects of the method, the fasteners 228 can provide the dual purpose of locking the adjustment assembly 220 and becoming implanted into the bone.

According yet another method of reconstructing a resectioned portion of a bone, the configuration of a reconstruction device 300, as shown in the embodiment of FIGS. 5A-B, may be moving the links 304 to achieve a desired directional and angular orientation in the manner described above. The orientation of each of the linkage 302 can be adapted simultaneously or separately. Whether the configuration of each link 304 is adapted simultaneously or separately, the linkages 302 should be configured such that at least some of the apertures 310 of one linkages 302 are aligned with at least some of the apertures 310 of the opposing linkage 302. The orientations of the linkages 302 are achieved by actuating the adjustment assembly 320. Once the adjustment assembly 320 has been adapted to a final configuration, the locking assembly 322 is actuated to an engaged configuration, whereby the linkages 302 are set more rigidly. Next, the reconstruction device 300 may be implanted by inserting the fasteners 328 into the bone to be reconstructed. Alternatively, linkages 302 may be aligned, coupled, and implanted in a single step. For example, the reconstruction device 300 may be positioned over the bone to be reconstructed, such that the apertures 310 of the linkages 302 are aligned, and the fasteners may be inserted through holes the apertures 310 and into the bone to implant the reconstruction device 300 and affix the orientation of the linkages 302.

The embodiments described in connection with the illustrated embodiments have been presented by way of illustration, and the present invention is therefore not intended to be limited to the disclosed embodiments. Accordingly, those skilled in the art will realize that the invention is intended to encompass all modifications and alternative arrangements included within the spirit and scope of the invention, as set forth by the appended claims.

What is claimed:

1. A reconstruction device configured for securement to a bone, the reconstruction device comprising:
an elongate linkage including at least a first link and a second link that is connected to the first link along an axis of elongation that extends along a substantially longitudinal direction, each link defining a one-piece body, wherein each link defines 1) a channel that extends through the one-piece body along the longitudinal direction, 2) an aperture that extends through the one-piece body along a vertical direction that is substantially perpendicular to the longitudinal direction, wherein a portion of the channel is open to the aperture, 3) a tongue that extends from a first end of the one-piece body along the longitudinal direction, and 4) a recess that extends into a second end of the one-piece body opposite the first end;
an adjustment assembly that provides for movement of the first and second links relative to each other in at least one of 1) a directional orientation about an axis that extends in the vertical direction and 2) an angular orientation about an axis that extends in the longitudinal direction, the adjustment assembly including a flexible connector slidably received in the channel of each link such that a portion of the connecter protrudes into the aperture, wherein the recess of one of the first and second links is configured to receive the tongue of the other of the first and second links so as to guide the movement of the first and second links relative to each other; and
a locking assembly operable between a disengaged configuration that allows for adjustment of the at least one of the directional and angular orientation of the first link relative to the second link and an engaged configuration that inhibits adjustment of the at least one of the directional orientation and the angular orientation of the first link relative to the second link, the locking assembly including a locking member configured for insertion through the aperture, wherein the locking member is configured to apply a biasing force to the connector, the biasing force having a directional component that extends along a horizontal direction that is perpendicular to the vertical direction.

2. The reconstruction device as recited in claim 1, wherein the locking member is configured to impart the biasing force directly onto the connector.

3. The reconstruction device as recited in claim 1, wherein the locking member comprises a fastener configured to directly engage the connector.

4. The reconstruction device as recited in claim 1, wherein the locking member imparts the biasing force indirectly onto the connector.

5. The reconstruction device as recited in claim 4, further comprising an insert disposed within the aperture, the insert configured to receive the locking member.

6. The reconstruction device as recited in claim 5, wherein the insert is angularly adjustable within the aperture.

7. The reconstruction device in claim 5, wherein the biasing force captures the connector between the insert and the link.

8. The reconstruction device as recited in claim 1, wherein the channel is coextensive with the aperture.

9. The reconstruction device as recited in claim 1, wherein the channel is disposed at one lateral end of the links, and a plurality of spine segments attaches the plurality of links at an opposing lateral end.

10. The reconstruction device as recited in claim 1, wherein each link further comprises a second channel extending therethrough, and the adjustment assembly includes a second connecting member slidably received in the second channel, such that the locking member imparts a biasing force onto both connectors.

11. The reconstruction device as recited in claim 10, wherein each of the first and second connectors have a pair of lateral portions, wherein one of the pair of lateral portions of the first and second connectors protrude into the aperture.

12. The reconstruction device as recited in claim 11, wherein the lateral portion of the first connector protrudes into the aperture to the same extent that the lateral portion of the second connector protrudes into the aperture.

13. The reconstruction device as recited in claim 1, wherein the locking member is a screw having a shaft, wherein a portion of the shaft is configured to engage a bone.

14. The reconstruction device as recited in claim 13, wherein the shaft is threaded.

15. The reconstruction device in claim 14, wherein when the locking assembly is in the engaged configuration the threaded shaft of the locking member contacts the connector.

16. The reconstruction device in claim 15, wherein the threaded shaft comprises a distal portion and a proximal portion that is opposite the distal portion, the distal portion having a shaft diameter and the proximal portion having a head diameter that is greater than the shaft diameter, and wherein the proximal portion of the threaded shaft contacts the connector.

17. The reconstruction device as recited in claim 1, wherein the locking member is a screw having a shaft, the shaft having a first portion and a second portion, the first portion of the shaft is configured to engage the aperture, and the second portion of the shaft is configured to engage a bone underlying the reconstruction device.

18. The reconstruction device as recited in claim 1, wherein the connector extends along the longitudinal horizontal, the connector defining a pair of lateral portions spaced apart along a lateral direction that is perpendicular to the longitudinal direction and the vertical direction, wherein one of the pair of lateral portions protrude into the aperture.

19. The reconstruction device in claim 11, wherein the locking member is angularly adjustable within the aperture and is further configured to engage the bone when the locking assembly is in the engaged configuration and the disengaged configuration.

20. The reconstruction device in claim 1, wherein the channel defines a first cross-sectional dimension and the connector defines a second cross-sectional dimension that is less than the first cross-sectional dimension such that the connector can slide and flex within the channel.

21. The reconstruction device in claim 1, wherein the horizontal direction includes the longitudinal direction.

22. The reconstruction device in claim 1, wherein the horizontal direction includes a lateral direction that is perpendicular to the longitudinal direction and the vertical direction.

23. The reconstruction device in claim 22, wherein the connector defines a connector central axis that is aligned with the longitudinal direction, and the locking member defines a locking member central axis that is aligned with the vertical direction, wherein when the locking member is inserted in the aperture, the locking member applies the biasing force to the connector along a lateral axis that is aligned with the lateral direction, the lateral axis being perpendicular to and intersecting the connector central axis and the locking member central axis.

24. The reconstruction device in claim 22, wherein the channel is a first channel, and the one-piece body further defines a second channel that extends from the first end to the second end along the longitudinal direction, the second channel spaced from the upper and lower surfaces, the second channel spaced from the first channel along the lateral direction, wherein the adjustment assembly includes a second connector configured to be slidably received in the second channel, wherein the locking member imparts a biasing force to the first and second connectors.

25. The reconstruction device in claim 1, wherein the recess and the tongue accommodate adjustment of the at least one of the directional or angular orientation of the first link relative to the second link while maintaining direct contact between the first and second links.

26. The reconstruction device in claim 1, wherein the tongue is integral to the one-piece body.

27. The reconstruction device in claim 1, wherein the tongue is attached to the one-piece body via a mechanical fastener.

28. The reconstruction device in claim 1, wherein the tongue is flexible so as to accommodate bending or twisting of the link to a desired directional and angular orientation.

29. The reconstruction device in claim 1, wherein the portion defines a first dimension in the vertical direction, and the connector defines a second dimension in the vertical direction that is greater than the first dimension.

30. The reconstruction device in claim 1, wherein the tongue has a vertical outer edge that is substantially planar to the vertical direction, the vertical outer edge configured to prevent angular movement of the first and second links about a lateral axis that extends along a lateral direction that is perpendicular to the vertical direction and the longitudinal direction.

\* \* \* \* \*